(12) United States Patent
Hosotani et al.

(10) Patent No.: US 12,263,015 B2
(45) Date of Patent: Apr. 1, 2025

(54) IN-VIVO IMPLANTABLE ELECTRONIC DEVICE

(71) Applicant: Murata Manufacturing Co., Ltd., Kyoto-fu (JP)

(72) Inventors: Tatsuya Hosotani, Nagaokakyo (JP); Kiyokazu Yamada, Nagaokakyo (JP)

(73) Assignee: Murata Manufacturing Co., Ltd., Kyoto-fu (JP)

( * ) Notice: Subject to any disclaimer, the term of this patent is extended or adjusted under 35 U.S.C. 154(b) by 985 days.

(21) Appl. No.: 17/160,064

(22) Filed: Jan. 27, 2021

(65) Prior Publication Data

US 2021/0145362 A1 May 20, 2021

Related U.S. Application Data

(63) Continuation of application No. PCT/JP2019/016303, filed on Apr. 16, 2019.

(30) Foreign Application Priority Data

Sep. 27, 2018 (JP) .................................. 2018-181758

(51) Int. Cl.
*A61B 5/00* (2006.01)
*A61L 31/02* (2006.01)
(Continued)

(52) U.S. Cl.
CPC ............ *A61B 5/686* (2013.01); *A61B 5/0026* (2013.01); *A61B 5/0031* (2013.01);
(Continued)

(58) Field of Classification Search
CPC ..... A61B 5/686; A61B 5/0026; A61B 5/0031; A61B 5/0036; A61B 2560/02;
(Continued)

(56) References Cited

U.S. PATENT DOCUMENTS 6,505,077 B1 * 1/2003 Kast ..................... A61N 1/3787
607/61
8,391,987 B2 * 3/2013 Faraji ................. A61N 1/37518
607/54
(Continued)

FOREIGN PATENT DOCUMENTS

EP 3284515 A1 * 2/2018 ............. A61B 5/686
JP 07265442 A * 10/1995
(Continued)

OTHER PUBLICATIONS

An Office Action; "Notice of Reasons for Refusal," mailed by the Japanese Patent Office on Dec. 14, 2021, which corresponds to Japanese Patent Application No. 2020-547937 and is related to U.S. Appl. No. 17/160,064 with English translation.
(Continued)

*Primary Examiner* — Eun Hwa Kim
*Assistant Examiner* — Ana Veruska Guerrero
(74) *Attorney, Agent, or Firm* — Studebaker Brackett PLLC

(57) ABSTRACT

An in-vivo implantable electronic device includes a housing, a power reception coil, and an electronic circuit. The housing is formed of a biocompatible material and forms an internal space sealed. The power reception coil is disposed in the internal space of the housing and receives power by interacting with an electromagnetic field formed by an external electric field or magnetic field, or transmits an electromagnetic wave to the outside. The electronic circuit is disposed in the internal space, is connected to the power reception coil, and performs at least processing of an electric signal. The housing includes a first member in a box shape formed of a biocompatible metal material and having an opening, a second member formed of a biocompatible nonmetal material and having a shape that closes the open-
(Continued)

ing, a packing in an annular shape disposed between the first member and the second member.

20 Claims, 11 Drawing Sheets

(51) Int. Cl.
*A61L 31/08* (2006.01)
*H01F 27/28* (2006.01)
*H01F 38/14* (2006.01)
*H02J 7/02* (2016.01)
*H02J 50/00* (2016.01)
*H02J 50/12* (2016.01)
*H02J 50/80* (2016.01)
*A61N 1/04* (2006.01)
*A61N 1/05* (2006.01)
*A61N 1/08* (2006.01)
*A61N 1/36* (2006.01)
*H01F 27/24* (2006.01)
*H02J 50/70* (2016.01)

(52) U.S. Cl.
CPC ............ *A61L 31/022* (2013.01); *A61L 31/026* (2013.01); *A61L 31/028* (2013.01); *A61L 31/082* (2013.01); *H01F 27/28* (2013.01); *H01F 38/14* (2013.01); *H02J 7/02* (2013.01); *H02J 50/005* (2020.01); *H02J 50/12* (2016.02); *H02J 50/80* (2016.02); *A61B 5/0036* (2018.08); *A61B 2560/02* (2013.01); *A61B 2560/0219* (2013.01); *A61B 2560/0406* (2013.01); *A61L 31/024* (2013.01); *A61L 2400/18* (2013.01); *A61N 1/0472* (2013.01); *A61N 1/05* (2013.01); *A61N 1/0529* (2013.01); *A61N 1/056* (2013.01); *A61N 1/08* (2013.01); *A61N 1/3605* (2013.01); *A61N 1/36062* (2017.08); *H01F 27/24* (2013.01); *H02J 50/70* (2016.02)

(58) Field of Classification Search
CPC .... A61B 2560/0219; A61B 2560/0406; A61B 2562/16; A61L 31/022; A61L 31/026; A61L 31/028; A61L 31/082; A61L 31/024; A61L 2400/18; H01F 27/28; H01F 38/14; H02J 7/02; H02J 50/005; H02J 50/12; H02J 50/80; H02J 50/70; H02J 7/00034; H02J 2310/23; H02J 50/10; A61N 1/0472; A61N 1/05; A61N 1/0529; A61N 1/056; A61N 1/08; A61N 1/3605; A61N 1/36062; A61N 1/3787; H04B 5/26; H04B 5/72; H04B 5/79
See application file for complete search history.

(56) References Cited

U.S. PATENT DOCUMENTS

| | | | |
|---|---|---|---|
| 8,805,537 B1* | 8/2014 | Cong | A61N 1/3758 607/116 |
| 2003/0050549 A1* | 3/2003 | Sochor | H01R 24/58 607/116 |
| 2005/0203584 A1* | 9/2005 | Twetan | A61N 1/37229 607/36 |
| 2008/0294207 A1* | 11/2008 | Kast | A61N 1/37514 607/2 |
| 2010/0060431 A1* | 3/2010 | Stevenson | A61B 5/0031 340/10.1 |
| 2011/0029036 A1 | 2/2011 | Yamamoto et al. | |
| 2015/0244178 A1 | 8/2015 | Tang | |
| 2016/0199657 A1* | 7/2016 | Jiang | A61N 1/3787 607/61 |
| 2021/0152021 A1* | 5/2021 | Sakamoto | A61L 31/082 |

FOREIGN PATENT DOCUMENTS

| | | | |
|---|---|---|---|
| JP | H07-265442 A | 10/1995 | |
| JP | 2004-352268 A | 12/2004 | |
| JP | 2017-164192 A | 9/2017 | |
| JP | 2018-501021 A | 1/2018 | |
| WO | WO-2017210316 A1 * | 12/2017 | A61B 3/00 |

OTHER PUBLICATIONS

International Search Report issued in PCT/JP2019/016303; mailed Jul. 23, 2019.
Written Opinion issued in PCT/JP2019/016303; mailed Jul. 23, 2019.
Tatsuya Hosotani et al.; "MHz-Band Magnetic Coupling Wireless Power Transfer Technology for Small Appliances"; 2016 National Convention of the Institute of Electrical Engineers of Japan; Mar. 16-18, 2016; vol. 4; total 6 pages; Japan.

* cited by examiner

IN-VIVO IMPLANTABLE ELECTRONIC DEVICE

CROSS-REFERENCE TO RELATED APPLICATIONS

This application claims benefit of priority to International Patent Application No. PCT/JP2019/016303, filed Apr. 16, 2019, and to Japanese Patent Application No. 2018-181758, filed Sep. 27, 2018, the entire contents of each are incorporated herein by reference.

BACKGROUND

Technical Field

The present disclosure relates to an in-vivo implantable electronic device that is used by being embedded (implanted) in the body of, for example, a living person or animal.

Background Art

Japanese Unexamined Patent Application Publication No. 2017-164192 describes an in-vivo implantable medical device having structure in which power is supplied from the outside. The device includes a device main body, a power reception coil, a secondary battery, and an electronic circuit. The power reception coil, the secondary battery, and the electronic circuit are housed inside the device main body.

SUMMARY

The in-vivo implantable medical device described in Japanese Unexamined Patent Application Publication No. 2017-164192 is configured to perform power supply by magnetic field coupling between the power reception coil in the device and an external power transmission coil, but a specific configuration is not illustrated for supplying power while the device is isolated from an environment outside the device in a living body.

In general, sapphire, ruby, glass, ceramic, or the like, which is a material excellent in biocompatibility, is difficult to process as a housing. On the other hand, although a biocompatible material made of metal such as titanium is easy to process as a housing, when such a metal housing is used, it is not easy to form magnetic coupling through the housing. In addition, a problem arises in that an eddy current is generated in the metal housing by an external magnetic field, and the housing generates heat.

Accordingly, the present disclosure provides an in-vivo implantable electronic device in which an electromagnetic action acting with an external electromagnetic field is ensured while maintaining biocompatibility, air-tightness and water-tightness.

An in-vivo implantable electronic device of the present disclosure includes a housing, a coil for power or an antenna for a signal, and an electronic circuit. Alternatively, an in-vivo implantable electronic device of the present disclosure includes a housing, a coil for power, an antenna for a signal, and an electronic circuit. The housing is formed of a biocompatible material, and forms an internal space sealed. The coil is disposed in the internal space, interacts with an electromagnetic field formed by an external electric field or magnetic field, and receives power. Further, the antenna transmits an electric signal to the outside or receives an electric signal from the outside by using a radio wave. The electronic circuit is disposed in the internal space, is connected to the coil or the antenna, and performs at least processing of an electric signal. The housing is configured to include a first member in a box shape made of a biocompatible metal material and having an opening, a second member made of a biocompatible nonmetal material and having a shape that closes the opening, and a packing in an annular shape disposed between the first member and the second member.

According to this configuration, it is possible to interact with an external electromagnetic field with a biocompatible nonmetal material interposed therebetween. Further, ease in processing of the first member can compensate for difficulty in processing of the second member, and further, air-tightness and water-tightness can be ensured by the packing.

According to the present disclosure, an in-vivo implantable electronic device can be obtained in which an electromagnetic action acting with an external electromagnetic field is ensured while maintaining biocompatibility and air-tightness and water-tightness. Accordingly, for example, it is possible to transmit an electric signal to the outside or receive an electric signal from the outside by using a radio wave. In addition, it is possible to use an electronic circuit or an electronic component, which is not formed of a biocompatible material, inside a housing formed of a biocompatible material having a sealed internal space, and it is possible to use external electrical energy and external radio waves through the housing.

DETAILED DESCRIPTION

Figure 1:
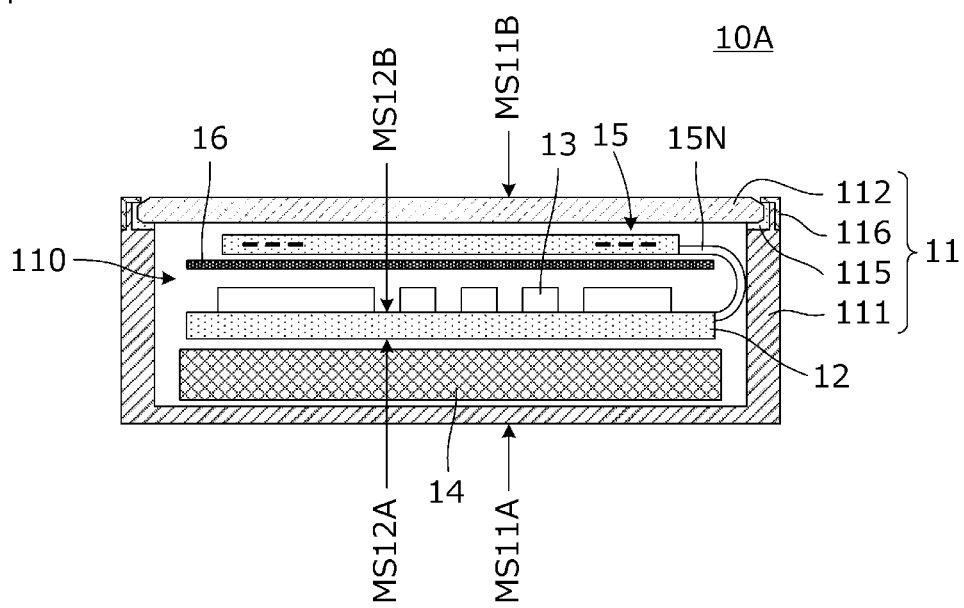
FIG. 1 is a sectional view of an in-vivo implantable electronic device according to a first embodiment.

Hereinafter, some specific examples will be illustrated with reference to the drawings, and a plurality of embodiments for implementing the present disclosure will be described. In the drawings, the same reference numerals are given to the same parts. In consideration of ease of description or understanding of main points, for convenience of description, description will be given as a plurality of embodiments, but partial substitutions or combinations of configurations described in different embodiments are possible. In a second and subsequent embodiments, descriptions of matters common to those in a first embodiment will be omitted, and only different points will be described. In particular, similar actions and effects according to similar configurations will not be described in detail for each embodiment.

First Embodiment

Figure 2:
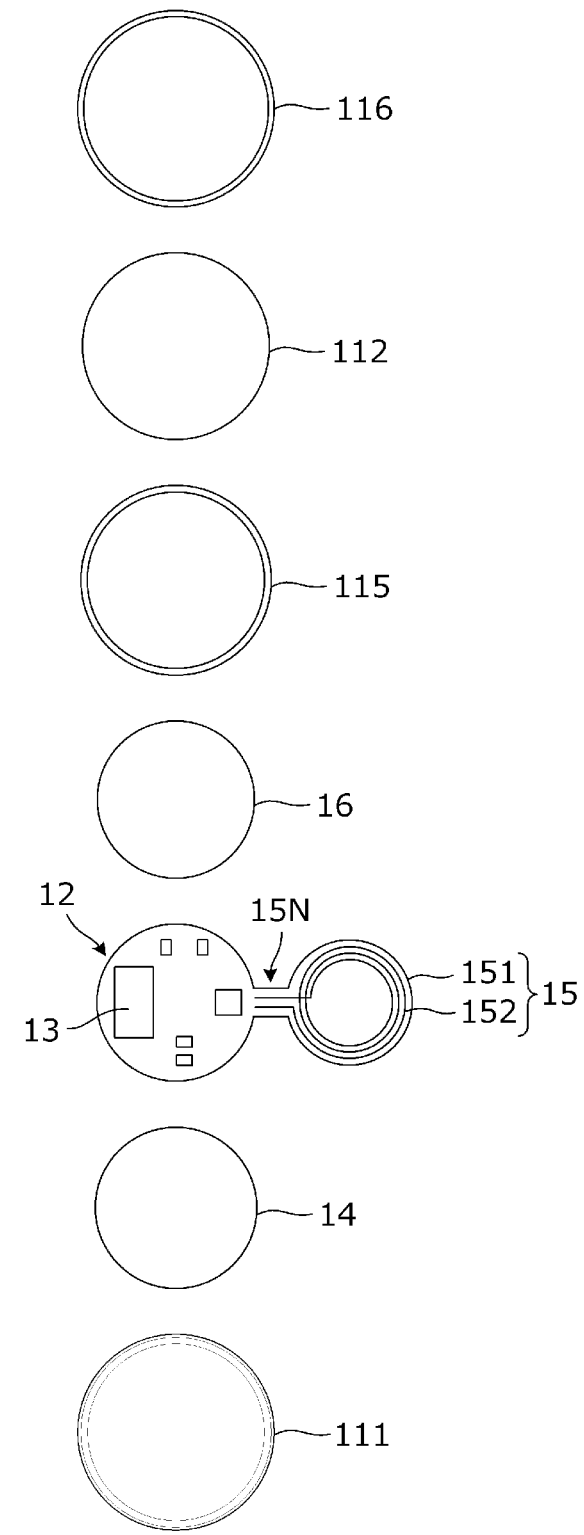
FIG. 2 is an exploded plan view of the in-vivo implantable electronic device.

FIG. 1 is a sectional view of the in-vivo implantable electronic device 10A according to a first embodiment. FIG. 2 is an exploded plan view of the in-vivo implantable electronic device 10A.

The in-vivo implantable electronic device 10A includes the housing 11, a circuit board 12, an electronic circuit component 13, a secondary battery 14, a power reception coil 15, and a magnetic material 16. The secondary battery 14 corresponds to a "power storage device" of the present disclosure.

The housing 11 is constituted by the first member 111, a second member 112, the fixing ring 116, and the packing 115. The fixing ring 116 is an example of a "fixing member" according to the present disclosure. The first member 111 is constituted by a disk-shaped bottom plate portion and a cylindrical side wall portion. The second member 112 has a disk-like shape. The second member 112 is fitted into an opening of the first member 111 with the packing 115 interposed therebetween. Detailed structure of a fitting portion of the second member 112 fit into the first member 111 will be described later. As described above, the housing 11 has a thin cylindrical can shape having an internal space 110 formed by combining the first member 111 and the second member 112 with each other with the packing 115 interposed therebetween. In the present embodiment, a lower surface of the first member 111 is referred to as a first main surface MS11A of the housing 11, and an upper surface (outer surface) of the second member 112 is referred to as a second main surface MS11B of the housing 11.

The first member 111 is a molded body of a biocompatible metal material. For example, the first member 111 is made of Ti (pure titanium) or a Ti alloy such as Ti-6A1-4V. Alternatively, the first member 111 is a sintered material of mixture of ceramic powder and powder of the above titanium alloy. By using such a biocompatible metal material for the first member 111, it is possible to suppress an influence on a living body and an influence from a living body.

As described above, the biocompatible metal material is preferably a material containing Ti as a main component, however, as the biocompatible metal material, a material such as stainless steel containing Cr or Mo, a Co—Cr alloy, or the like may be used. Note that, it is preferable that the biocompatible metal material be a material having durability against an environment, stress, and the like, and for example, the biocompatible metal material is more preferably a material having a Young's modulus of 100 GPa or more.

The second member 112 is a molded body of a biocompatible nonmetal material. For example, the second member 112 is made of sapphire, ruby, glass, ceramic, or the like. By using such a biocompatible nonmetal material for the second member 112, it is possible to suppress an influence on a living body and an influence from a living body.

Note that, in view of the durability against the environment, the above-described ceramic is preferably fine ceramics using a material such as sapphire or ruby represented by the chemical formula $Al_2O_3$.

In addition, when attention is focused on easiness in processing, it is preferable to use glass as a biocompatible nonmetal material.

The packing 115 is a material having more flexibility than the first member 111 and the second member 112, and is a molded body of a synthetic polymer compound having a main skeleton by a siloxane bond, such as silicone rubber. For example, a silicone oil or the like is applied, as a biocompatible oil, to the packing 115.

The circuit board 12, the electronic circuit component 13, the secondary battery 14, the power reception coil 15, and the magnetic material 16 are disposed in the internal space 110 of the housing 11. Note that, in the following description, the power reception coil 15 and the magnetic material 16 are described as being separate from each other, however, the magnetic material 16 may be configured as part of the power reception coil 15.

The circuit board 12 is constituted by an insulating base body on which a predetermined conductor pattern is formed, and the electronic circuit component 13 mounted on the insulating base body. This circuit board 12 includes a main circuit for realizing a function of the in-vivo implantable electronic device 10A.

The circuit board 12 is a flat plate and has a first main surface MS12A and a second main surface MS12B. The circuit board 12 is disposed such that the first main surface MS12A and the second main surface MS12B are substantially parallel to the first main surface MS11A and the second main surface MS11B of the housing 11. In addition, the second main surface MS12B of the circuit board 12 is on a side of the second main surface MS11B of the housing 11, and the first main surface MS12A of the circuit board 12 is on a side of the first main surface MS11A of the housing 11.

A plurality of the electronic circuit components 13 is provided for realizing the function of the in-vivo implantable electronic device 10A, and includes, for example, various kinds of biological sensors, ICs, passive elements, and the like. That is, the plurality of electronic circuit components 13 is a component of an "electronic circuit" that performs the signal processing of the present disclosure. The plurality of electronic circuit components 13 is mounted on the second main surface MS12B of the circuit board 12 and is connected to a conductor pattern of the circuit board 12.

Note that, in plan view of the second main surface MS12B of the circuit board 12, a position where the plurality of electronic circuit components 13 is disposed preferably overlaps at least part of a region of the power reception coil 15 defined by an outer shape of the power reception coil 15, and it is more preferable that all the electronic circuit components 13 be within the above-described region. This makes it possible to reduce a planar shape of the first main surface MS11A or the second main surface MS11B of the housing 11 and to reduce the size of the in-vivo implantable electronic device 10A.

The secondary battery 14 is a known chargeable and dischargeable battery, and is disposed along the first main surface MS12A of the circuit board 12. The secondary battery 14 preferably has a thin shape. The secondary battery 14 is connected to the conductor pattern of the circuit board 12.

As illustrated in FIG. 2, the power reception coil 15 and the circuit board 12 are integrally formed as a single multilayer substrate. The power reception coil 15 is a planar coil, and is constituted by a base material 151 that has an insulating property and a coil conductor 152. The power reception coil 15 is connected to the circuit board 12 with a base portion 15N thereof interposed therebetween. The coil conductor 152 of the power reception coil 15 is connected to the conductor pattern of the circuit board 12. The base portion 15N of the power reception coil has the number of layers of base materials smaller than the number of layers of a portion of the power reception coils 15 and the number of layers of a portion of the circuit board 12, and has flexibility.

The coil conductor 152 is a conductor pattern in which a main portion is formed in a spiral shape of one layer. Note that, the coil conductor 152 may be formed in a plurality of layers.

As illustrated in FIG. 1, the power reception coil 15 is disposed on a side of the second main surface MS12B of the circuit board 12. The power reception coil 15 is disposed such that a surface where the coil conductor 152 is formed and the second main surface MS11B of the housing 11 are parallel to each other.

The magnetic material 16 is a disk-shaped magnetic sheet. The magnetic material 16 is disposed between the power reception coil 15 and the second main surface MS12B of the circuit board 12. The magnetic material 16 is disposed such that a main surface thereof is parallel to the surface where the coil conductor 152 is formed. It is preferable that the magnetic material 16 be in contact with the power reception coil 15.

Since the power reception coil 15 is separated from the secondary battery 14, and the magnetic material 16 is disposed between the power reception coil 15 and the secondary battery 14, substantially no magnetic flux interlinked with a coil opening of the power reception coil 15 reaches the secondary battery, and substantially no eddy current is generated in an electrode of the secondary battery 14, thereby suppressing generation of heat and a decrease in power receiving efficiency of the power reception coil 15 due to an eddy current.

Figure 3:
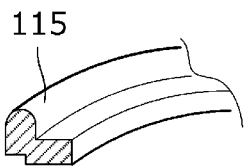
FIG. 3 is a cutaway perspective view that illustrates a shape of a packing.
Figure 4A:
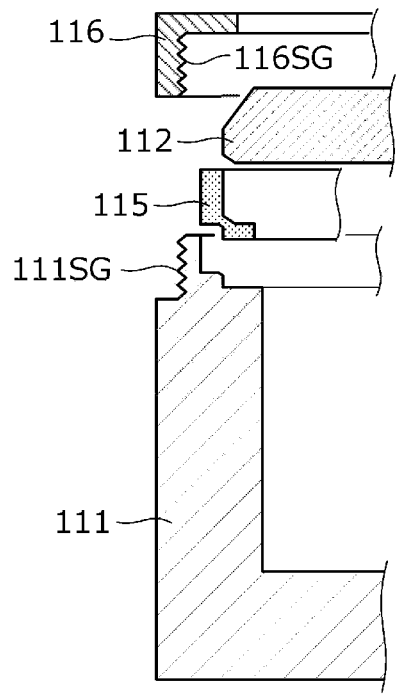
FIG. 4A and FIG. 4B are partial sectional views illustrating structure of a fitting portion of a second member and the like fit into an opening of a first member of a housing.
Figure 4B:
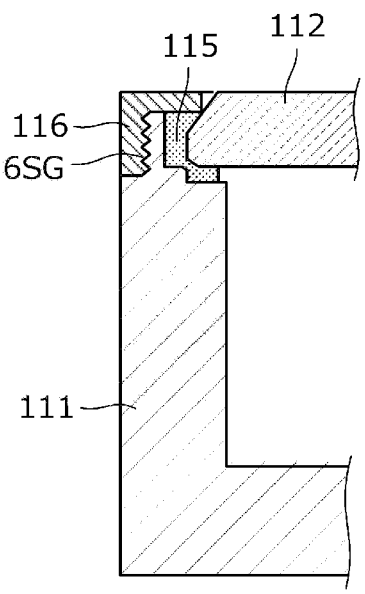

FIG. 3 is a cutaway perspective view that illustrates a shape of the above packing 115. FIG. 4A and FIG. 4B are partial sectional views illustrating structure of a fitting portion of the second member 112 and the like fit into an opening of the first member 111 of the housing 11. FIG. 4A is the partial sectional view in a state before the first member 111 and the second member 112 of the housing 11, the fixing ring 116, and the packing 115 are combined with each other. FIG. 4B is the partial sectional view in a state in which the parts are combined with each other.

As illustrated in FIG. 2, FIG. 4A, and FIG. 4B, the fixing ring 116 in an annular shape is provided and holds the second member 112 in a direction in which the second member 112 is fitted into the opening of the first member 111. A screw groove 111SG is formed in an outer peripheral edge of the opening of the first member 111. That is, an external thread is formed in the opening of the first member 111.

An outline of the fixing ring 116 is an annular shape, and a cross-section in a radial direction from a center of the annular shape is an L-shape. A screw groove 116SG is formed in an inner peripheral edge of this fixing ring 116. That is, an internal thread is formed in the fixing ring 116. This screw groove 116SG of the fixing ring 116 is screwed into the screw groove 111SG of the first member 111.

In the state illustrated in FIG. 4A, the packing 115 is attached to an inner peripheral edge of the opening of the first member 111, the second member 112 is placed thereon, and the fixing ring 116 is put thereon further from above, and the screw groove 111SG of the first member 111 is screwed into the screw groove 116SG of the fixing ring 116. Thereby, the second member 112 is pressed toward the first member 111, and the packing 115 is pressed between the first member 111 and the second member 112. The packing 115 is more flexible than the first member 111 and the second member 112, and thus is deformed, and is in close contact with an outer peripheral edge of the second member 112 while being in close contact with the first member 111. Thereby, the structure illustrated in FIG. 4B is obtained.

The fixing ring 116 is made of a biocompatible metal material. For example, similarly to the first member 111, the fixing ring 116 is made of Ti or a Ti alloy such as Ti-6A1-4V.

The packing 115 is made of a biocompatible nonmetal material. For example, silicone rubber for medical applications that does not include organic plasticizers is used, and liquid silicone rubber (LSR) and high-temperature vulcanized silicone rubber (HCR, HTV) are used.

Figure 5:
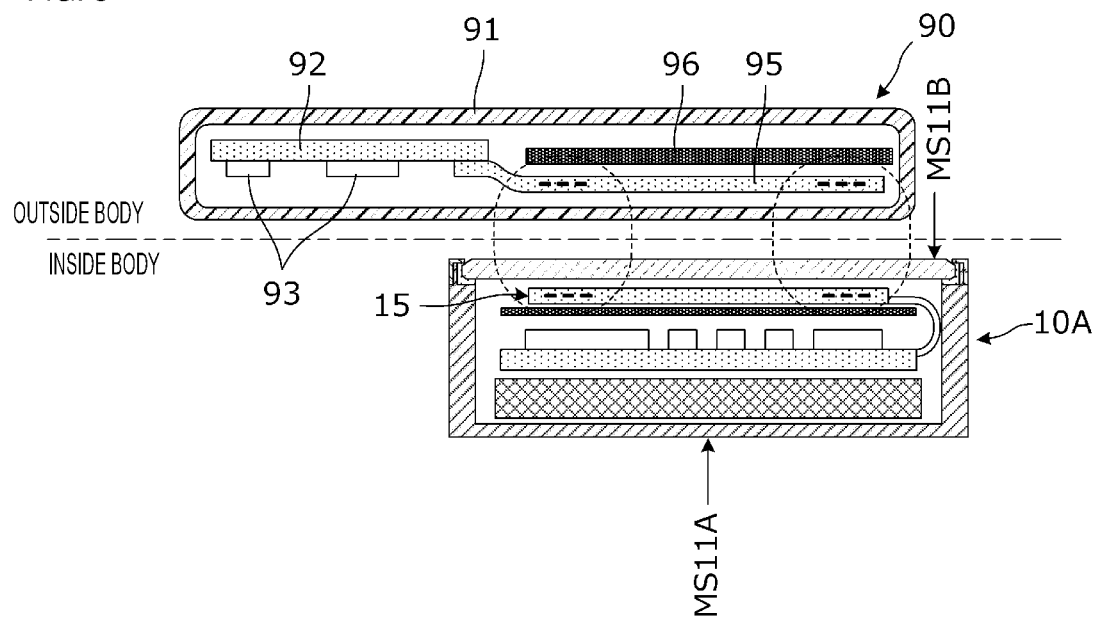
FIG. 5 is a sectional view illustrating a configuration of a power transmission device that transmits power to the in-vivo implantable electronic device.

FIG. 5 is a sectional view illustrating a configuration of a power transmission device that transmits power to the in-vivo implantable electronic device 10A. FIG. 5 is a sectional view illustrating a state in which the power transmission device is brought close to the in-vivo implantable electronic device 10A.

The in-vivo implantable electronic device 10A illustrated in FIG. 5 is disposed in a living body, and the power transmission device 90 is disposed outside the living body.

The in-vivo implantable electronic device 10A is disposed such that the second main surface MS11B is a side facing a surface of a body (a side facing from the inside of a living body toward the outside of the living body), and the first main surface MS11A is a side facing the inside of the living body.

The power transmission device 90 includes a housing 91, a circuit board 92, an electronic circuit component 93, a power transmission coil 95, and a magnetic material 96.

The housing 91 has a box-like shape. The housing 91 is made of a nonmetal material such as resin. The circuit board 92, the electronic circuit component 93, the power transmission coil 95, and the magnetic material 96 are disposed in an internal space of the housing 91.

A circuit for realizing a function of the power transmission device 90 is included in the circuit board 92.

A plurality of the electronic circuit components 93 is provided for realizing the function of the power transmission device 90, and includes various types of power supply ICs, passive elements, and the like. The plurality of electronic circuit components 93 is mounted on one main surface of the circuit board 92, and is connected to a conductor pattern of the circuit board 92.

The power transmission coil 95 includes a base material and a coil conductor. The base material is a thin plate having an insulating property. Further, the coil conductor is a conductor pattern formed in a spiral shape. The coil conductor is formed on one main surface of the base material. The power transmission coil 95 is disposed side by side with respect to the circuit board 92. A coil conductor of the power transmission coil 95 is connected to the circuit board 92. Note that, in the present embodiment, the coil conductor of the power transmission coil 95 includes a single layer, but may include a plurality of layers.

The magnetic material 96 is a disk-shaped magnetic sheet. The magnetic material 96 is disposed on one main surface side of the power transmission coil 95. Preferably, the magnetic material 96 is in contact with the power transmission coil 95.

The power transmission device 90 is disposed close to the in-vivo implantable electronic device 10A such that the power transmission coil 95 has a predetermined positional relationship with the power reception coil 15. At this time, the power transmission device 90 is disposed such that the magnetic material 96 is located on a side opposite to the power reception coil 15 with respect to the power transmission coil 95.

In such a state, the power reception coil 15 and the power transmission coil 95 disposed are magnetically coupled to each other, and power is supplied from the power transmission device 90 to the in-vivo implantable electronic device 10A. This power is stored in the secondary battery 14 and supplied to the electronic circuit component 13 and the like.

In the example illustrated in FIG. 5, a region where the coil conductor of the power transmission coil 95 is formed and a region where a coil conductor of the power reception coil 15 is formed substantially entirely overlap each other in plan view, and are close to each other.

Figure 6:
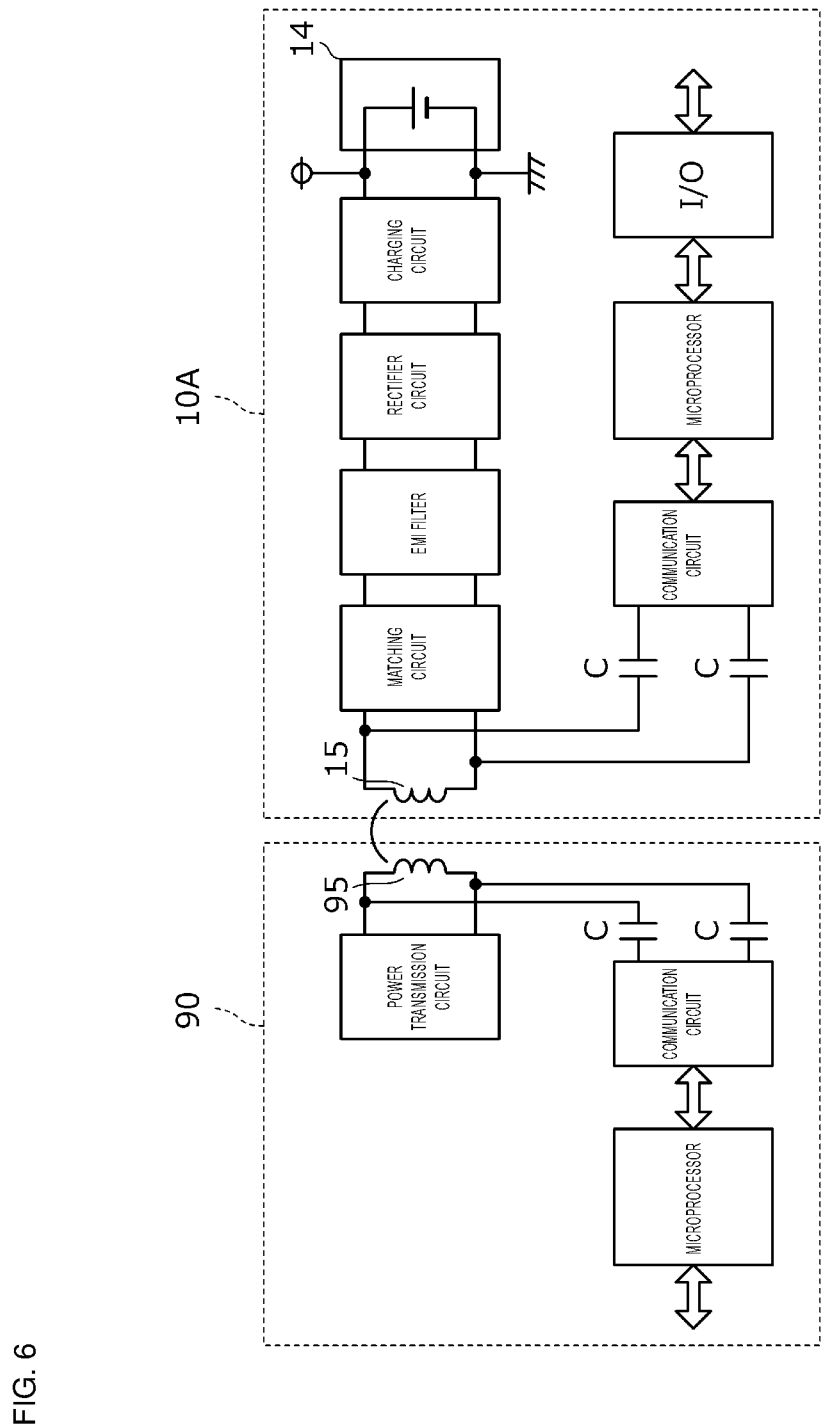
FIG. 6 is a block diagram illustrating a circuit configuration of a power supply system constituted by the in-vivo implantable electronic device and a power transmission device.

FIG. 6 is a block diagram illustrating a circuit configuration of a power supply system constituted by the in-vivo implantable electronic device 10A and a power transmission device 90. The power transmission device 90 is provided with the power transmission coil 95, a power transmission circuit connected thereto, a communication circuit, a microprocessor, and the like. The in-vivo implantable electronic device 10A is provided with the power reception coil 15, a matching circuit, an EMI filter, a rectifier circuit, a charging circuit, and the secondary battery 14. These circuits constitute a circuit of a power supply system. In addition, the in-vivo implantable electronic device 10A is provided with a communication circuit, a microprocessor, and an I/O circuit. These circuits constitute circuits of a signal processing system and an arithmetic system. The above communication circuit is connected to the power reception coil 15 with a capacitor C interposed therebetween.

The above rectifier circuit rectifies a current/voltage induced in the power reception coil, and the EMI filter removes an electromagnetic noise component. The rectifier circuit rectifies a received alternating current/voltage to a direct current. The charging circuit performs charge control of the secondary battery 14 with DC power outputted from the rectifier circuit.

The above I/O circuit inputs and outputs signals to and from various sensors connected thereto. The microprocessor performs predetermined signal processing and arithmetic processing. The communication circuit outputs data to external devices such as a power transmission device, other measurement devices, and a medical care device. This is performed by superimposing a signal in a predetermined format on a current flowing in the power reception coil 15.

Second Embodiment

In a second embodiment, an example of an in-vivo implantable electronic device including a biological sensor outside a main body of the in-vivo implantable electronic device will be illustrated.

Figure 7:
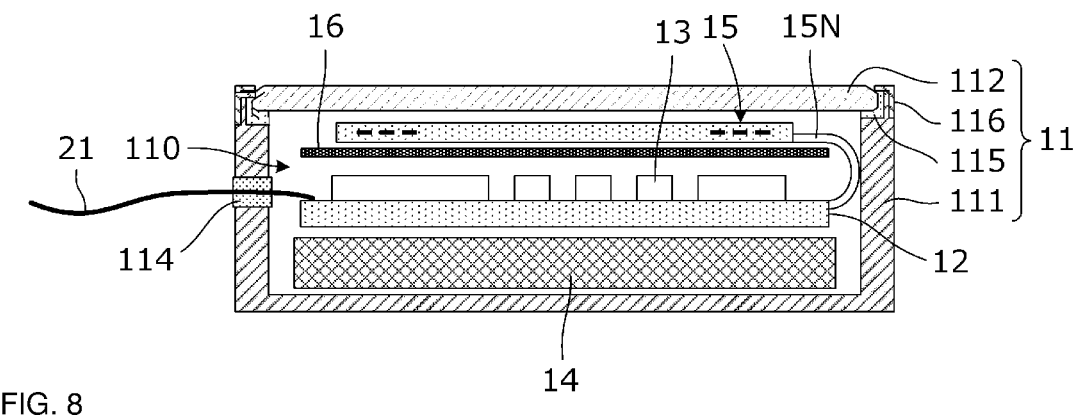
FIG. 7 is a sectional view of an in-vivo implantable electronic device according to a second embodiment.
Figure 8:
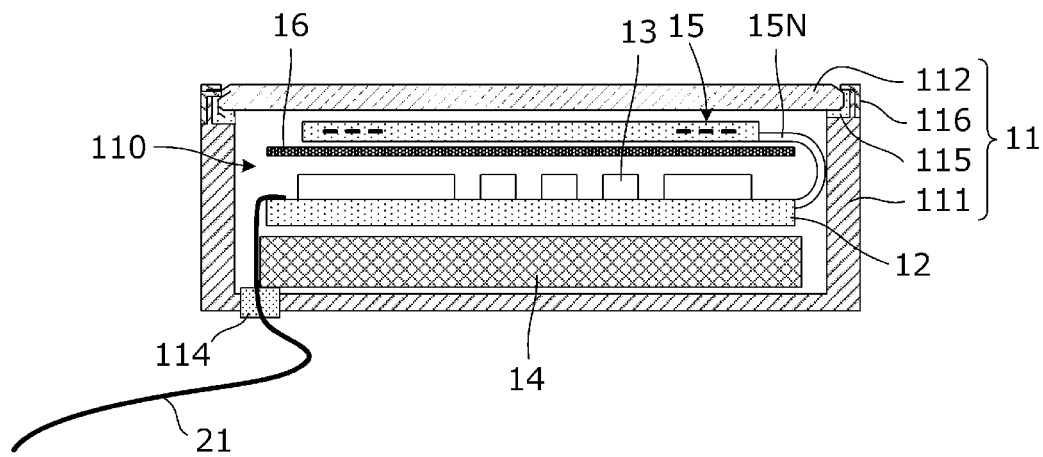
FIG. 8 is a sectional view of an in-vivo implantable electronic device according to the second embodiment.
Figure 9:
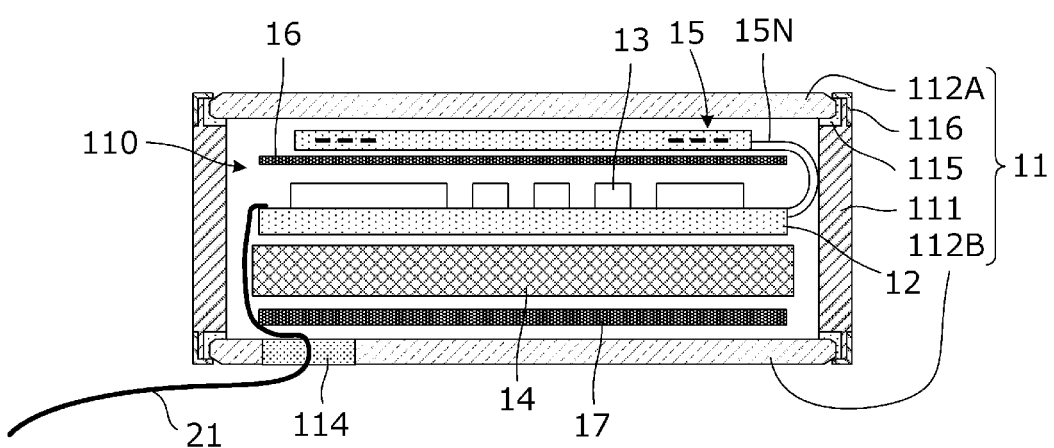
FIG. 9 is a sectional view of an in-vivo implantable electronic device according to the second embodiment.

FIG. 7 is a sectional view of the in-vivo implantable electronic device 10B according to the second embodiment, FIG. 8 is a sectional view of the in-vivo implantable electronic device 10C according to the second embodiment, and FIG. 9 is a sectional view of the in-vivo implantable electronic device 10D according to the second embodiment.

The in-vivo implantable electronic device 10B illustrated in FIG. 7 is provided with a feedthrough 114 in a cylindrical sidewall portion of the first member 111 of the housing 11. A biological sensor 21 itself has a linear shape and extends outside the housing 11 through the feedthrough 114.

The biological sensor 21 is connected to the circuit board 12 in the housing 11 through the feedthrough 114.

The feedthrough 114 is disposed at a position away from the power reception coil 15 in the housing 11. In the example illustrated in FIG. 7, the feedthrough 114 is disposed at a position where the magnetic material 16 is interposed between the feedthrough 114 and the power reception coil 15.

The in-vivo implantable electronic device 10C illustrated in FIG. 8 is provided with the feedthrough 114 in a disk-shaped bottom plate portion of the first member 111 of the housing 11. Other configurations are similar to those in the in-vivo implantable electronic device 10B illustrated in FIG. 7.

The in-vivo implantable electronic device 10D illustrated in FIG. 9 includes the housing 11, the circuit board 12, the electronic circuit component 13, the secondary battery 14, the power reception coil 15, the magnetic material 16, and a magnetic material 17.

The housing 11 is constituted by the first member 111, second members 112A and 112B, the fixing ring 116, and the packing 115. The first member 111 has a cylindrical shape. The second members 112A and 112B each have a disk-like shape. The second members 112A and 112B are respectively fitted into two openings in the first member 111, with the packing 115 interposed therebetween. Further, the feedthrough 114 is provided in part of the second member 112B.

With such a configuration, the biological sensor 21 can be disposed outside the housing 11, and a degree of freedom in disposition of the biological sensor 21 is improved. Also, even when a main part of the feedthrough 114 is made of a metal material, the feedthrough 114 is disposed at a position magnetically separated from the power reception coil 15, and thus, magnetic coupling between the power reception coil 15 and the power transmission coil 95 (see, for example, FIG. 5) is not inhibited.

Note that, since the magnetic material 17 is disposed closer to an outside than the secondary battery 14 and the circuit board 12, even when strength of a magnetic field on a side of the second member 112B is high for some reason, an induced current flowing through the secondary battery 14 or a conductor pattern of the circuit board 12 by the magnetic field from the outside is suppressed. Further, the magnetic material 17 constitutes part of a magnetic path suitable for forming magnetic coupling between the power reception coil 15 and the power transmission coil 95.

Third Embodiment

In a third embodiment, an example of an in-vivo implantable electronic device including an antenna that transmits an electric signal to an outside or receives an electric signal from the outside will be described.

Figure 10:
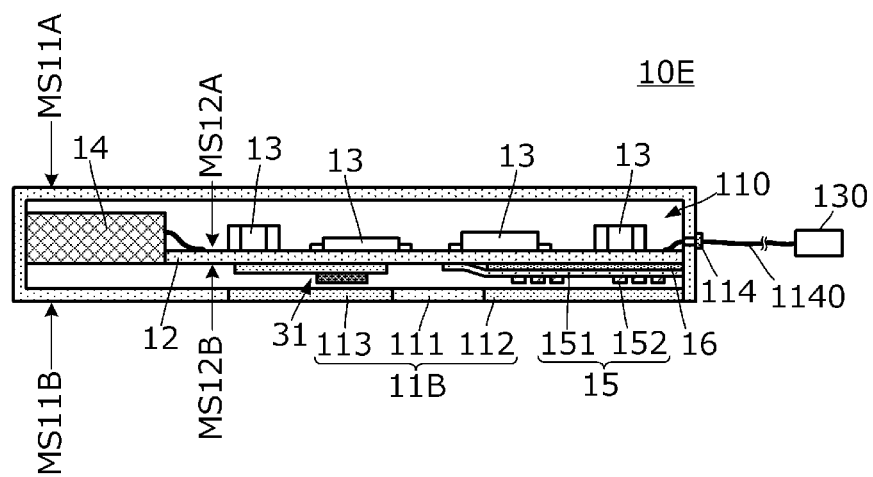
FIG. 10 is a sectional view of an in-vivo implantable electronic device according to a third embodiment.

FIG. 10 is a sectional view of the in-vivo implantable electronic device 10E according to the third embodiment. The in-vivo implantable electronic device 10E includes a housing 11B, the circuit board 12, the electronic circuit component 13, the secondary battery 14, the power reception coil 15, and the magnetic material 16.

The housing 11B includes the first member 111, the second member 112, and a third member 113. The housing 11B forms a thin box-like shape by combining the first member 111, the second member 112, and the third member 113 together. The housing 11B has the first main surface MS11A and the second main surface MS11B. The first main surface MS11A and the second main surface MS11B are separated from each other in a height direction of the housing 11B, are each orthogonal to the height direction, and face each other.

The first member 111 has a box-like shape having an opening in part of the second main surface MS11B, and the second member 112 has a flat plate shape. The second member 112 is fitted into the opening of the first member 111.

A cylindrical side wall portion of the first member 111 of the housing 11B is provided with the feedthrough 114. A biological sensor 130 is connected to the outside of the housing 11 via the feedthrough 114 and a cable 1140.

With such a configuration, the biological sensor 130 can be disposed outside the housing 11B, and a degree of freedom in disposition of the biological sensor 130 is improved. At this time, since the feedthrough 114 is disposed on a side of the first main surface MS12A of the circuit board 12, formation of an electromagnetic resonance field is not inhibited.

In addition, the in-vivo implantable electronic device 10E includes a built-in communication module 31. The built-in communication module 31 is mounted on the second main surface MS12B of the circuit board 12. The built-in communication module 31 is separated from the power reception coil 15, and in plan view, is disposed such that a communication antenna of the built-in communication module 31 overlaps the third member 113.

The built-in communication module 31 includes a planar communication antenna that transmits an electric signal to an outside or receives an electric signal from the outside, and a communication IC. These are mounted or formed in a circuit board for the built-in communication module 31. Communication realized by the built-in communication module 31 is data communication. This communication is realized with near field communication, such as MICS in a 400 MHz band, Wi-Fi for a 2.4 GHz band, Bluetooth (registered trademark) for the 2.4 GHz band, Bluetooth Low Energy (registered trademark) for the 2.4 GHz band, Wi-Fi for a 5.0 GHz band, and the like, and power consumption thereof is preferably low.

Figure 11:
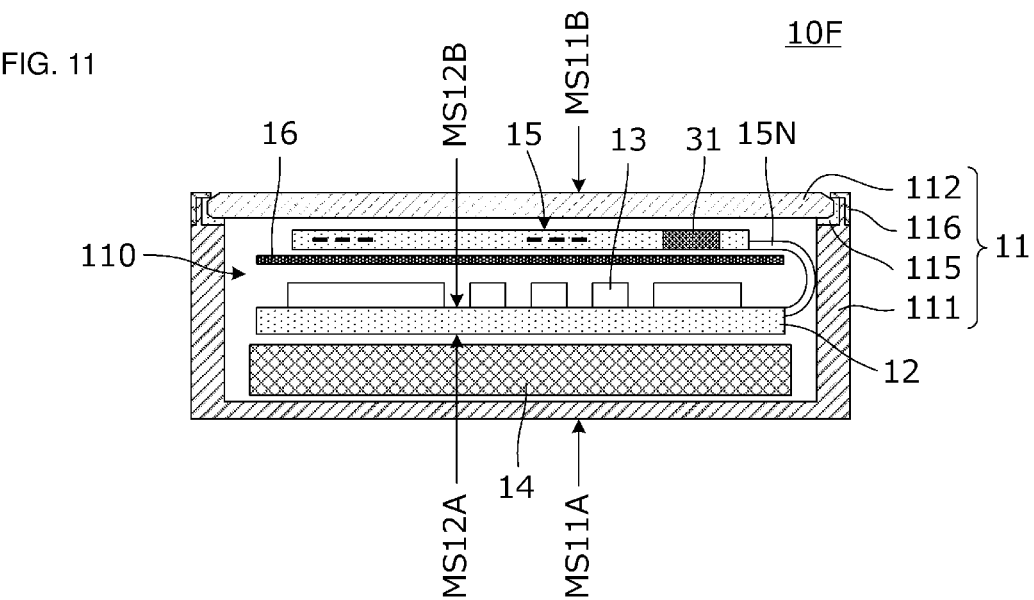
FIG. 11 is a sectional view of another in-vivo implantable electronic device 10F according to the third embodiment.

FIG. 11 is a sectional view of another in-vivo implantable electronic device 10F according to the third embodiment. The in-vivo implantable electronic device 10F includes the housing 11, the circuit board 12, the electronic circuit component 13, the secondary battery 14, the power reception coil 15, the magnetic material 16, and the built-in communication module 31. The built-in communication module 31 is provided in the power reception coil 15. The built-in communication module 31 is located outside a winding region of a coil conductor of the power reception coil 15 and is separated from the coil conductor. Other configurations are similar to those in the in-vivo implantable electronic device 10A illustrated in the first embodiment.

Figure 12:
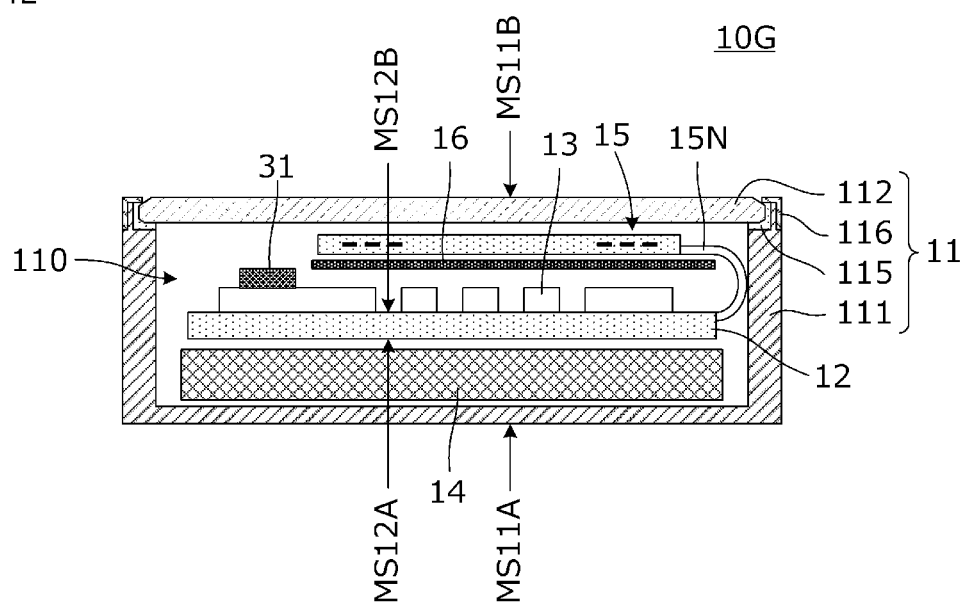
FIG. 12 is a sectional view of yet another in-vivo implantable electronic device 10G according to the third embodiment.

FIG. 12 is a sectional view of yet another in-vivo implantable electronic device 10G according to the third embodiment. The in-vivo implantable electronic device 10G includes the housing 11, the circuit board 12, the electronic circuit component 13, the secondary battery 14, the power reception coil 15, the magnetic material 16, and the built-in communication module 31. The built-in communication module 31 is mounted on the circuit board 12. The magnetic material 16 and a coil conductor of the power reception coil 15 are not present above the built-in communication module 31. That is, since a communication antenna of the built-in communication module 31 is not covered with the magnetic material 16 and the coil conductor of the power reception coil 15, communication can be performed on a side of the second main surface MS11B of the housing 11.

Fourth Embodiment

In a fourth embodiment, another example of structure of a fitting portion between a first member and a second member of a housing will be illustrated.

Figure 13A:
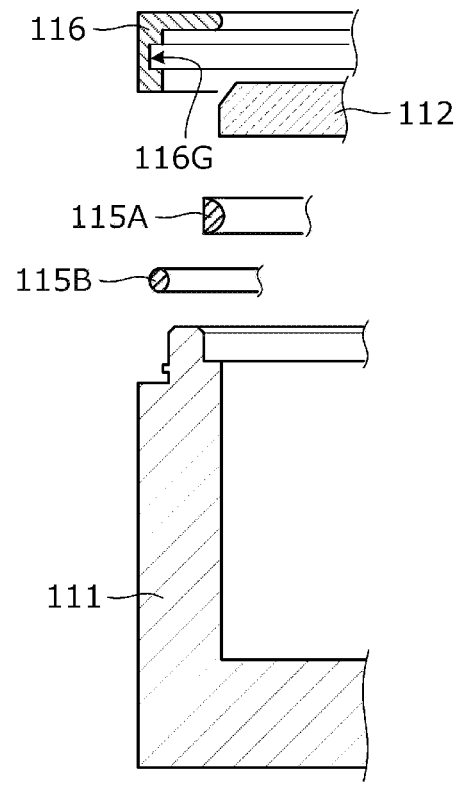
FIG. 13A and FIG. 13B are partial sectional views illustrating structure of a fitting portion of a second member and the like fit into an opening of the first member of the housing, in an in-vivo implantable electronic device according to a fourth embodiment.
Figure 13B:
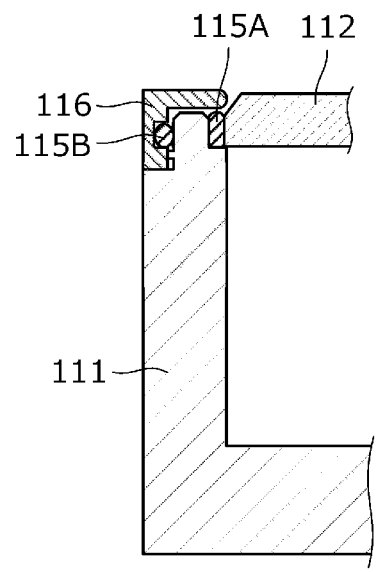

FIG. 13A and FIG. 13B are partial sectional views illustrating structure of a fitting portion of the second member 112 or the like fit into an opening of the first member 111 of the housing 11. FIG. 13A is the partial sectional view in a state before the first member 111 and the second member 112 of the housing 11, the fixing ring 116, and packings 115A and 115B are combined with each other. FIG. 13B is the partial sectional view in a state in which those parts are combined with each other.

As illustrated in FIG. 13A, the fixing ring 116 in an annular shape is provided and holds the second member 112 in a direction in which the second member 112 is fitted into the opening of the first member 111. An outline of the fixing ring 116 is an annular shape, and a cross-section in a radial direction from a center of the annular shape is an L-shape. A groove 116G is formed in an inner peripheral edge of the fixing ring 116.

In the state illustrated in FIG. 13A, the packing 115B is attached to the groove 116G of the fixing ring 116, the packing 115A is attached to an inner peripheral edge of an opening of the first member 111, the second member 112 is placed thereon, the fixing ring 116 is put thereon further from above, and the fixing ring 116 is screwed into an outer periphery of the opening of the first member 111. In this state, as illustrated in FIG. 13B, the packing 115B is sandwiched between the groove 116G of the fixing ring 116 and an outer peripheral edge of the opening of the first member 111. Further, the packing 115A is sandwiched between the inner peripheral edge of the opening of the first member 111 and an outer peripheral edge of the second member 112.

FIG. 14A, FIG. 14B, FIG. 14C, and FIG. 14D are views illustrating other shapes of packings sandwiched between a peripheral edge of the first member 111 and the second member 112 or sandwiched between the opening of the first member 111 and the fixing ring 116. Packings of various shapes can be used as a packing that is sandwiched between the peripheral edge of the opening of the first member 111 and the second member 112 or between the opening of the first member 111 and the fixing ring 116.

Figures 14A, 14B, 14C, 14D:
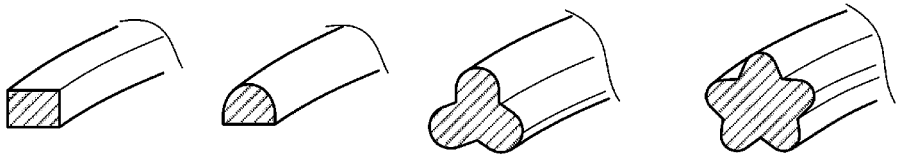
FIGS. 14A, 14B, 14C, and 14D are views illustrating other shapes of packings sandwiched between a peripheral edge of an opening of the first member and a second member, or sandwiched between the opening of the first member and a fixing ring.

As illustrated in FIG. 14A, a packing having a rectangular cross-section in a radial direction from a center of an annular shape may be used. The cross-section in the radial direction from the center of the annular shape may have a semicircular shape having a plane parallel to an annular circumferential surface. As illustrated in FIG. 14C and FIG. 14D, the cross-section in the radial direction from the center of the annular shape may have a flower-like shape having a plurality of petals.

Fifth Embodiment

A fifth embodiment illustrates an in-vivo implantable electronic device that forms an electromagnetic resonance field between a power reception coil of the in-vivo implantable electronic device and a power transmission coil that is external to a housing thereof and receives power from the power transmission coil.

Figure 15:
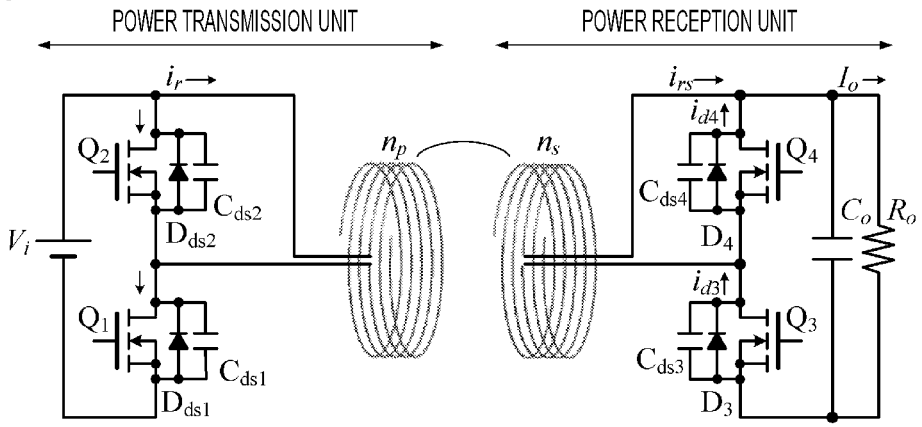
FIG. 15 is a circuit diagram of a power supply system constituted by a power reception unit of an in-vivo implantable electronic device according to a fifth embodiment and an external power transmission unit.
Figure 16:
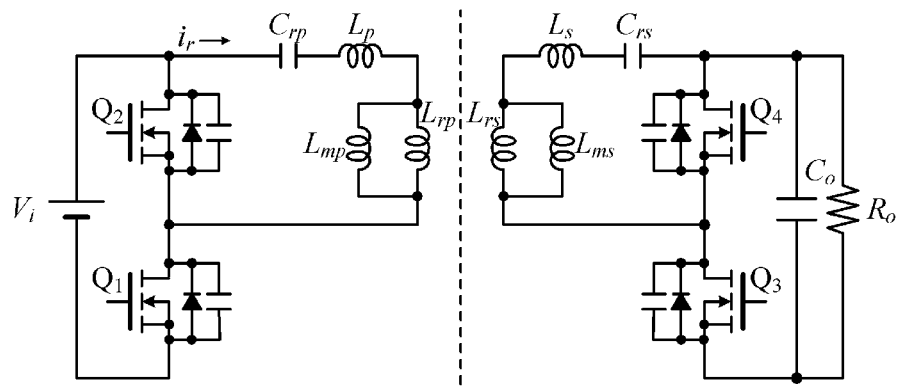
FIG. 16 is an equivalent circuit diagram of the power supply system illustrated in FIG. 15.
Figure 17:
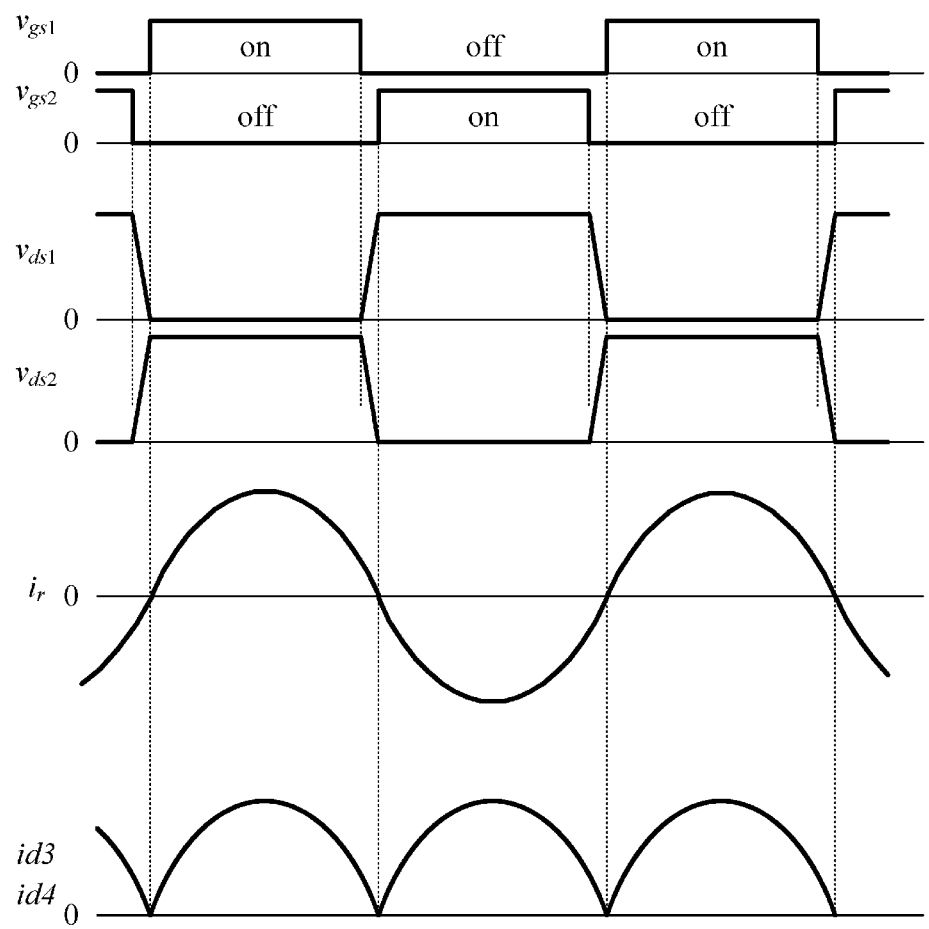
FIG. 17 is a waveform diagram of voltage/current in each section in FIG. 15 and FIG. 16.

FIG. 15 is a circuit diagram of a power supply system constituted by a power reception unit of the in-vivo implantable electronic device according to the fifth embodiment and an external power transmission unit. FIG. 16 is an equivalent circuit diagram of the power supply system illustrated in FIG. 15. Further, FIG. 17 is a waveform diagram of voltage/current in each section in FIG. 15 and FIG. 16.

An input unit of the power transmission unit includes an input power supply Vi. The power transmission unit includes a power transmission coil np and an alternating current generation circuit electrically connected to the power transmission coil np. The power reception unit includes a power reception coil ns and a power reception circuit electrically connected to the power reception coil ns.

Each of the power transmission coil np and the power reception coil ns is a helical coil, and a center portion of each of the power transmission coil np and the power reception coil ns serves as an input/output portion. Thus, the power transmission coil np has equivalent inductances Lp, Lmp, and Lrp, and equivalent capacitance Crp, and these constitute a resonance circuit. Similarly, the power reception coil ns has inductances Ls, Lms, and Lrs, and capacitance Crs, and these constitute a resonance circuit. Respective winding axes of the two helical coils are substantially aligned (substantially coaxial) with each other, and thus, between the power transmission coil np and the power reception coil ns, electric field energy and magnetic field energy interact, thereby forming an electromagnetic resonance field.

A power transmission alternating current generating circuit includes a first switching circuit equivalently constituted by a parallel connection circuit of a first switching element Q1, a diode Dds1, and a capacitor Cds1 and a second switching circuit equivalently constituted by a parallel connection circuit of a second switching element Q2, a diode Dds2, and a capacitor Cds2.

The switching elements Q1 and Q2 are subjected to switching control by a switching control circuit (not illustrated). In FIG. 17, Vgs1 is a gate-source voltage signal of the first switching element Q1, and Vgs2 is a gate-source voltage signal of the second switching element Q2. As illustrated in FIG. 17, the first switching element Q1 and the second switching element Q2 are alternately turned on and off, thereby supplying an alternating voltage/alternating current to the power transmission coil np.

The above switching control circuit switches the first switching element Q1 and the second switching element Q2 at a predetermined operating frequency, thereby intermittently supplying a direct current voltage to the above resonance circuit, and generating a resonance current. This makes a voltage across both ends of the first switching circuit and the second switching circuit have a sinusoidal waveform of half-wave for each half cycle. For example, switching operation is performed in 6.78 MHz or 13.56 MHz, which is an International ISM (Industrial, Scientific and electronic) band.

The power reception unit includes a power reception rectification circuit by switching elements Q3 and Q4 for rectifying an alternating current generated in the power reception coil ns, and a smoothing capacitor Co.

The switching elements Q3 and Q4 are controlled by a switching control circuit (not illustrated), and rectification is performed in synchronization with changes in a direction of a resonance current flowing through the power reception coil ns, and a direct current is supplied to a load Ro.

In a system in which wireless power supply is performed by electromagnetic resonance coupling, unlike a system in which a high-frequency magnetic field is applied to a resonator, a process of the power supply can be simplified and a power loss can be reduced.

Finally, the description of the embodiments described above is illustrative in all respects and is not restrictive. Those skilled in the art can appropriately make modifications and variations. The scope of the present disclosure is indicated by the appended claims rather than by the foregoing embodiments. Further, the scope of the present disclosure includes modifications from the embodiments within the scope of the claims.

Aspects

Aspects disclosed by the embodiments of the present disclosure described above will be listed below.
(Aspect 1)
The in-vivo implantable electronic device 10A or the like includes the housing 11 formed of a biocompatible material and configured to form an internal space sealed, a coil 15 for power reception disposed in the internal space and configured to interact with an electromagnetic field formed by an external electric field or magnetic field and receive power or a coil 15 as an antenna disposed in the internal space and configured to transmit an electric signal to an outside or receive an electric signal from the outside using a radio wave, and an electronic circuit disposed in the internal space, connected to the coil 15, and configured to perform at least processing of an electric signal. The housing 11 is configured to include the first member 111 in a box shape made of a biocompatible metal material and having an opening, the second member 112 made of a biocompatible nonmetal material and having a shape that closes the opening, the packing 115 in an annular shape disposed between the first member 111 and the second member 112, and the like.

According to this configuration, it is possible to interact with the external electromagnetic field with the biocompatible nonmetal material interposed therebetween. Further, ease in processing of the first member 111 can compensate for difficulty in processing of the second member 112, and further, air-tightness and water-tightness can be secured by the packing 115 and the like.
(Aspect 2)
The in-vivo implantable electronic device 10A or the like includes the housing 11 formed of a biocompatible material and configured to form an internal space sealed, the coil 15 for power reception disposed in the internal space and configured to interact with an electromagnetic field formed by an external electric field or magnetic field and receive power, an antenna for communication configured to transmit an electric signal to an outside or receive an electric signal from the outside, and an electronic circuit disposed in the internal space, connected to the coil 15 for power reception and the antenna for communication, and configured to perform at least processing of an electric signal. The housing 11 is configured to include the first member 111 in a box-shape made of a biocompatible metal material and having an opening, the second member 112 made of a biocompatible nonmetal material and having a shape that closes the opening, the packing 115 in an annular shape disposed between the first member 111 and the second member 112, and the like.

(Aspect 3)

A fixing member 116 in an annular shape made of a biocompatible metal material is provided in the opening of the first member 111 of the housing 11 of the in-vivo implantable electronic device 10A and the like and holds the second member 112 in a direction in which the second member 112 is fitted. With this structure, attachment strength of the second member 112 to the first member 111 can be easily increased.

(Aspect 4)

The first member 111 and the fixing member 116 of the in-vivo implantable electronic device 10A and the like respectively have the grooves 111SG and 116SG for screw fitting at contact portions where the first member and the fixing member being in contact with each other. With this structure, attachment strength of the second member 112 to the first member 111 and sealability can be easily increased.

(Aspect 5)

The packing 115 and the like of the in-vivo implantable electronic device 10A and the like are made of a biocompatible nonmetal material. This makes it possible to reduce an influence of the in-vivo implantable electronic device on a living body and an influence of a living body on the implantable electronic device, even when the packing 115 and the like come into contact with the living body.

(Aspect 6)

The above packing 115 and the like are made of a synthetic polymer compound having a main skeleton by a siloxane bond. This makes it possible to maintain high compatibility with a living body and high sealability.

(Aspect 7)

A cross-section in a radial direction from a center of the annular shape of the packing 115 or the like is a substantially L-shape. This makes it possible to increase a bonding area between an inner peripheral edge of the opening of the first member 111 and an outer peripheral edge of the second member 112, and to obtain high sealability of the housing 11.

(Aspect 8)

A biocompatible oil is applied to the packing 115 or the like. This increases sealability by the packing 115 or the like.

(Aspect 9)

A biocompatible metal material of the in-vivo implantable electronic device 10A or the like is a material containing Ti or a titanium alloy made of Ti-6A1-4V as a main component. This makes it possible to further suppress an influence on a living body and an influence from a living body.

(Aspect 10)

A biocompatible metal material of the in-vivo implantable electronic device 10A or the like is a sintered material of a mixture of ceramic powder and powder of the above-described titanium alloy. This makes it possible to form the biocompatible metal material which is difficult to process into a free shape. Further, by adjusting a material or an amount of blending, it is possible to adjust ease of processing and hardness. Further, a processing cost can be reduced.

(Aspect 11)

A biocompatible nonmetal material of the in-vivo implantable electronic device 10A or the like is sapphire, ruby, glass, or ceramic. This makes it possible to further suppress an influence on a living body and an influence from a living body. Note that, a second member formed of the biocompatible nonmetal material can have a simple plate shape, and thus, it is also possible to use such a material having low processability.

(Aspect 12)

The power reception coil 15 of the in-vivo implantable electronic device 10A or the like forms an electromagnetic resonance field between the power reception coil 15 and the power transmission coil 95 outside the housing 11 and receives power from the power transmission coil 95. This suppresses leakage of an electromagnetic field to the outside of the electromagnetic resonance field. Thus, it is possible to effectively suppress adverse effects due to an electromagnetic field generated for power transmission on the circuit board 12 and the electronic circuit component 13 of the in-vivo implantable electronic device 10A or the like and a living body in which the in-vivo implantable electronic device 10A or the like is embedded.

(Aspect 13)

The magnetic material 16 that constitutes part of a magnetic path of magnetic flux interlinked with the power reception coil 15 is provided in the housing 11 of the in-vivo implantable electronic device 10A or the like on a surface side opposite to the outside. Accordingly, substantially no magnetic flux interlinked with a coil opening of the power reception coil reaches a member, such as a secondary battery or a circuit board, inside the housing 11, and an induced current is not generated in the secondary battery or a conductor pattern of the circuit board, and thus heat generation and a decrease in power receiving efficiency of the power reception coil 15 due to an induction current are suppressed.

(Aspect 14)

A power storage device for storing power received by the power reception coil 15 is provided in the housing 11 of the in-vivo implantable electronic device 10A or the like. This makes it possible to drive an electronic circuit with a stable power supply voltage stored in the power storage device.

What is claimed is:

1. An in-vivo implantable electronic device, comprising:
a housing including a biocompatible material and configured to define an internal space sealed;
a coil disposed in the internal space and configured to interact with an electromagnetic field generated by an external electric field or magnetic field and receive power, or an antenna disposed in the internal space and configured to transmit an electric signal to an outside or receive an electric signal from an outside by using a radio wave; and
an electronic circuit disposed in the internal space, connected to the coil or the antenna, and configured to perform at least processing of an electric signal,
wherein the housing is configured to include
a first member in a box shape made of a biocompatible metal material and having an opening,
a second member made of a biocompatible nonmetal material and having a shape that closes the opening, and a flexible packing in an annular shape disposed between the first member and the second member, wherein the flexible packing is disposed directly between the first member and the second member, wherein the second member comprises an upper surface, a lower surface, and an outer peripheral edge disposed between the upper surface and lower surface, and the flexible packing is in direct contact with the lower surface and the outer peripheral edge of the second member when viewed in cross section.

2. The in-vivo implantable electronic device according to claim 1, wherein the flexible packing is made of a biocompatible nonmetal material.

3. The in-vivo implantable electronic device according to claim 1, wherein the flexible packing is made of a synthetic polymer compound having a main skeleton by a siloxane bond.

4. The in-vivo implantable electronic device according to claim 1, wherein a cross-section in a radial direction from a center of the annular shape of the flexible packing is a substantially L-shape.

5. The in-vivo implantable electronic device according to claim 1, wherein a biocompatible oil is on the flexible packing.

6. The in-vivo implantable electronic device according to claim 1, wherein
the biocompatible metal material is a material containing Ti or a titanium alloy made of Ti-6A1-4V as a main component.

7. The in-vivo implantable electronic device according to claim 6, wherein
the biocompatible metal material is a sintered material of a mixture of ceramic powder and powder of the titanium alloy.

8. The in-vivo implantable electronic device according to claim 1, wherein
the biocompatible nonmetal material is sapphire, ruby, glass, or ceramic.

9. The in-vivo implantable electronic device according to claim 1, wherein
the coil generates an electromagnetic resonance field between the coil and a power transmission coil outside the housing and receives power from the power transmission coil.

10. The in-vivo implantable electronic device according to claim 1, further comprising:
a magnetic material configured to define, on a surface side in the housing opposite to the outside, part of a magnetic path of magnetic flux interlinked with the coil.

11. The in-vivo implantable electronic device according to claim 1, further comprising in the housing:
a power storage device configured to store power received by the coil.

12. An in-vivo implantable electronic device, comprising:
a housing including a biocompatible material and configured to define an internal space sealed;
a coil disposed in the internal space and configured to interact with an electromagnetic field generated by an external electric field or magnetic field and receive power;
an antenna configured to transmit an electric signal to an outside or receive an electric signal from an outside by using a radio wave; and
an electronic circuit disposed in the internal space, connected to the coil and the antenna, and configured to perform at least processing of an electric signal, wherein the housing is configured to include a first member in a box shape made of a biocompatible metal material and having an opening,
a second member made of a biocompatible nonmetal material and having a shape that closes the opening, and
a flexible packing in an annular shape disposed between the first member and the second member, wherein the flexible packing is disposed directly between the first member and the second member, wherein the second member comprises an upper surface, a lower surface, and an outer peripheral edge disposed between the upper surface and lower surface, and the flexible packing is in direct contact with the lower surface and the outer peripheral edge of the second member when viewed in cross section.

13. The in-vivo implantable electronic device according to claim 12, wherein
the housing includes a fixing member in an annular shape including a biocompatible metal material that holds the second member in a direction in which the second member is fitted into the opening of the first member.

14. The in-vivo implantable electronic device according to claim 12, wherein the flexible packing is made of a biocompatible nonmetal material.

15. The in-vivo implantable electronic device according to claim 12, wherein the flexible packing is made of a synthetic polymer compound having a main skeleton by a siloxane bond.

16. The in-vivo implantable electronic device according to claim 12, wherein a cross-section in a radial direction from a center of the annular shape of the flexible packing is a substantially L-shape.

17. The in-vivo implantable electronic device according to claim 12, wherein
the biocompatible metal material is a material containing Ti or a titanium alloy made of Ti-6A1-4V as a main component.

18. An in-vivo implantable electronic device, comprising:
a housing including a biocompatible material and configured to define an internal space sealed;
a coil disposed in the internal space and configured to interact with an electromagnetic field generated by an external electric field or magnetic field and receive power, or an antenna disposed in the internal space and configured to transmit an electric signal to an outside or receive an electric signal from an outside by using a radio wave; and
an electronic circuit disposed in the internal space, connected to the coil or the antenna, and configured to perform at least processing of an electric signal,
wherein the housing is configured to include
a first member in a box shape made of a biocompatible metal material and having an opening,
a second member made of a biocompatible nonmetal material and having a shape that closes the opening,
a flexible packing in an annular shape disposed between the first member and the second member, wherein the flexible packing is disposed directly between the first member and the second member, wherein the second member comprises an upper surface, a lower surface, and an outer peripheral edge disposed between the upper surface and lower surface, and the flexible packing is in direct contact with the lower surface and the outer peripheral edge of the second member when viewed in cross section, and
wherein the housing includes a fixing member in an annular shape including a biocompatible metal material that holds the second member in a direction in which the second member is fitted into the opening of the first member.

19. The in-vivo implantable electronic device according to claim 18, wherein
the first member and the fixing member respectively have grooves configured to screw-fit at contact portions where the first member and the fixing member are in contact with each other.

20. The in-vivo implantable electronic device according to claim 18, wherein the fixing member is in direct contact with the first member and the flexible packing when viewed in cross-section.

* * * * *